United States Patent
Fisher

(10) Patent No.: US 7,354,413 B2
(45) Date of Patent: Apr. 8, 2008

(54) DEVICE FOR TREATING FOOT DROP

(76) Inventor: Robert C. Fisher, 127 S. Central Ave., Wayzata, MN (US) 55391

( * ) Notice: Subject to any disclaimer, the term of this patent is extended or adjusted under 35 U.S.C. 154(b) by 177 days.

(21) Appl. No.: 11/265,633

(22) Filed: Nov. 2, 2005

(65) Prior Publication Data

US 2007/0100268 A1   May 3, 2007

(51) Int. Cl.
*A61F 5/00* (2006.01)
(52) U.S. Cl. .......................... 602/29; 602/23
(58) Field of Classification Search ............ 602/5, 602/23, 27–29; D24/192
See application file for complete search history.

(56) References Cited

U.S. PATENT DOCUMENTS

| | | | |
|---|---|---|---|
| 2,584,010 A | 1/1952 | Goffredo |
| 3,527,209 A | 9/1970 | Baker |
| 3,556,091 A | 1/1971 | Haig |
| 3,986,501 A | 10/1976 | Schad |
| 4,329,982 A | 5/1982 | Heaney |
| 4,459,980 A | 7/1984 | Perser et al. |
| 4,559,934 A | 12/1985 | Philipp |
| 4,566,447 A | 1/1986 | Deis |
| 4,817,589 A | 4/1989 | Wertz |
| 5,219,324 A | 6/1993 | Hall |
| 5,257,969 A | 11/1993 | Mance |
| 5,277,699 A | 1/1994 | Williamson |
| 5,291,904 A | 3/1994 | Walker |
| 5,382,224 A | 1/1995 | Spangler |
| 5,399,155 A | 3/1995 | Strassburg et al. |
| 5,609,568 A | 3/1997 | Andrews |
| 5,718,673 A | 2/1998 | Shipstead |
| 5,776,090 A | 7/1998 | Bergmann et al. |
| 5,860,423 A | 1/1999 | Thompson |
| 6,361,517 B1 | 3/2002 | Slinger |
| 6,602,217 B2 | 8/2003 | Crawford et al. |
| 6,695,797 B2 | 2/2004 | Trieloff |
| 2005/0038365 A1 | 2/2005 | Scott |

OTHER PUBLICATIONS

Dorsi-Strap™ Product Description, online, retrieved from http://x-strap.com/dorsi-strap.htm on Nov. 6, 2005.
"Foot Drop," James W. Pritchett, MD, FACS, *eMedicine* (online), Mar. 16, 2005, pp. 1-17, retrieved on Apr. 12, 2005 from http://www.emedicine.com/orthoped/topic389.htm.

*Primary Examiner*—Kim M Lewis
(74) *Attorney, Agent, or Firm*—Fredrikson & Byron, P.A.

(57) ABSTRACT

A foot support system includes a base to receive a sole of a foot, a cuff adapted to attach to a first portion of a leg near a knee of the leg, and a strap extending between the base and the cuff. The strap includes an elastic portion, a proximal segment attachable to the cuff, and a distal segment coupled to the base in proximity to a toe edge of the base. A strap holder may be included in certain embodiments of the invention to provide a relatively conforming fit to a wearer of the system, thereby allowing for a wider range of footwear options. An alternate embodiment of the invention may include a plurality of branches extending from the distal segment of the strap and adapted to fit between adjacent toes of a wearer in order to couple the strap to the base.

20 Claims, 4 Drawing Sheets

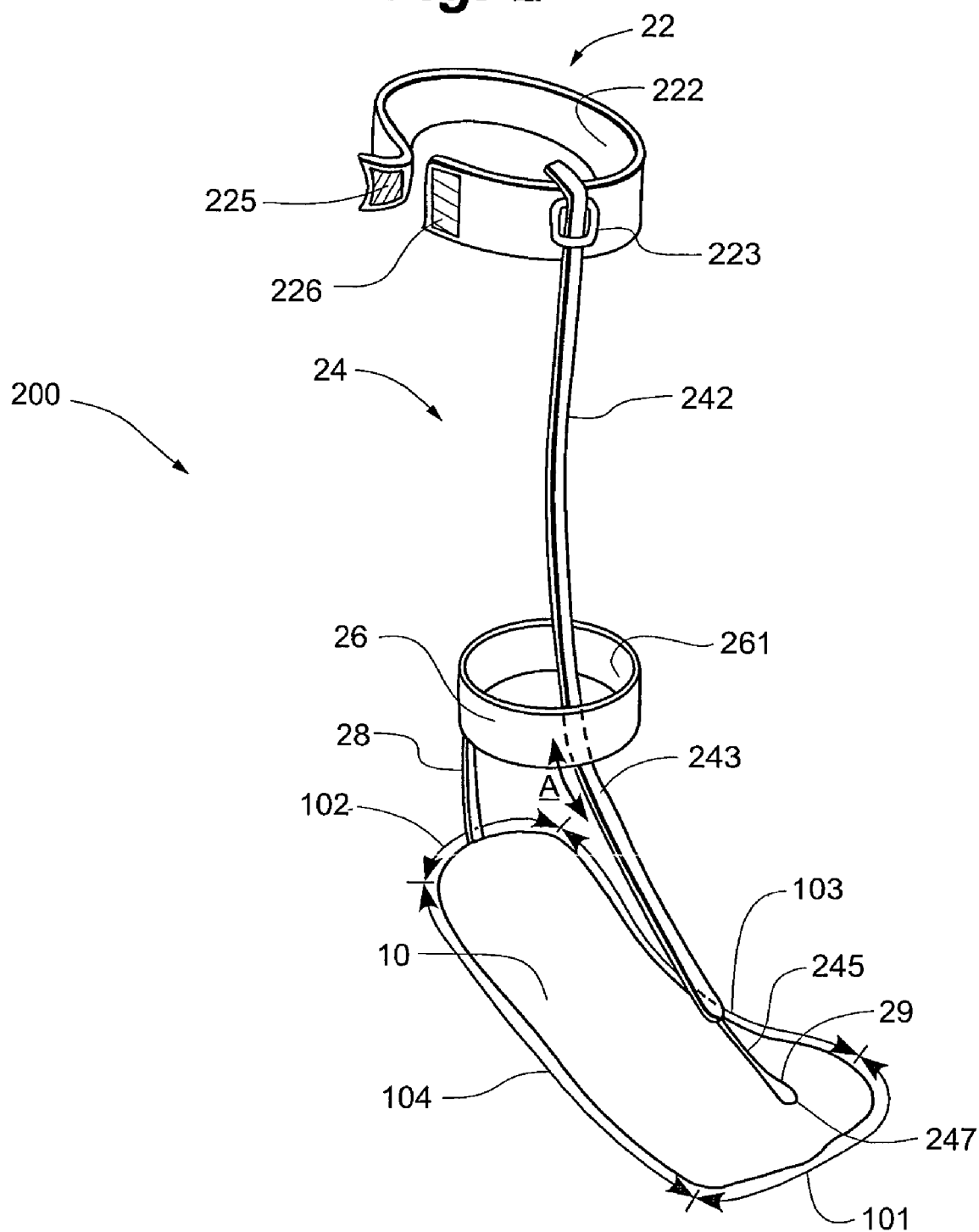

DEVICE FOR TREATING FOOT DROP

FIELD OF THE INVENTION

The invention relates generally to a foot support system for the treatment of foot drop.

BACKGROUND

Those suffering from "foot drop," also known as dorsi-flexion weakness of the foot, lack sufficient muscular control to move their foot upward relative to their lower leg (i.e., to dorsi-flex). Since the foot tends to hang in a downward (i.e., plantar-flexed) position, a person suffering from foot drop has a difficult time walking, having to use other muscles throughout the body to raise the knee and hip so that the forefoot will clear the ground during the swing phase of the gait cycle. Foot drop can be caused by a variety of conditions, including neurological diseases, and/or injuries to the brain, spinal cord, musculature, and peripheral nervous system, for example.

Devices exist to address the foot drop condition by holding the foot in a dorsi-flexed position. Such devices tend to be bulky and are noticeably visible to others, often requiring the use of specially modified footwear and/or attachments. A need exists for a foot support system that provides dorsi-flexion support while allowing plantar-flexion, and that conforms to the wearer's foot and leg to provide a more aesthetically pleasing range of footwear options to the wearer.

SUMMARY OF THE INVENTION

In certain embodiments of the invention, a foot support system includes a base adapted to receive a sole of a foot, a cuff that can be secured to a leg near the knee, and a strap including an elastic portion coupled to the cuff, and a plurality of branches coupled to the base near a toe edge of the base, each branch spaced apart from one another to allow passage of a toe between adjacent branches.

In another embodiment of the invention, a foot support system includes a base adapted to receive a sole of a foot, a cuff that can be secured to a leg near the knee, a strap including an elastic portion, the strap coupled to the cuff at a proximal end of the strap and coupled to a toe edge of the base near a distal end of the strap, and a strap holder secured to a leg near the ankle to retain the strap near the second portion of the leg.

In certain other embodiments of the invention, a foot support system includes a base adapted to receive a sole of a foot, a cuff that can be secured to a leg near the knee, a strap including an elastic portion, the strap coupled to the cuff at a proximal end of the strap and coupled to a toe edge of the base near a distal end of the strap, a strap holder secured to a leg near the ankle to retain the strap near the second portion of the leg, and a guide to facilitate movement of the strap along a length of the leg relative to the strap holder when the elastic portion of the strap stretches and contracts between the base and the cuff, a portion of the guide being positioned between the strap holder and the strap.

DESCRIPTION OF THE DRAWINGS

FIG. 2 is a top perspective view of a foot support system according to an embodiment of the invention.

DETAILED DESCRIPTION

Figure 1:
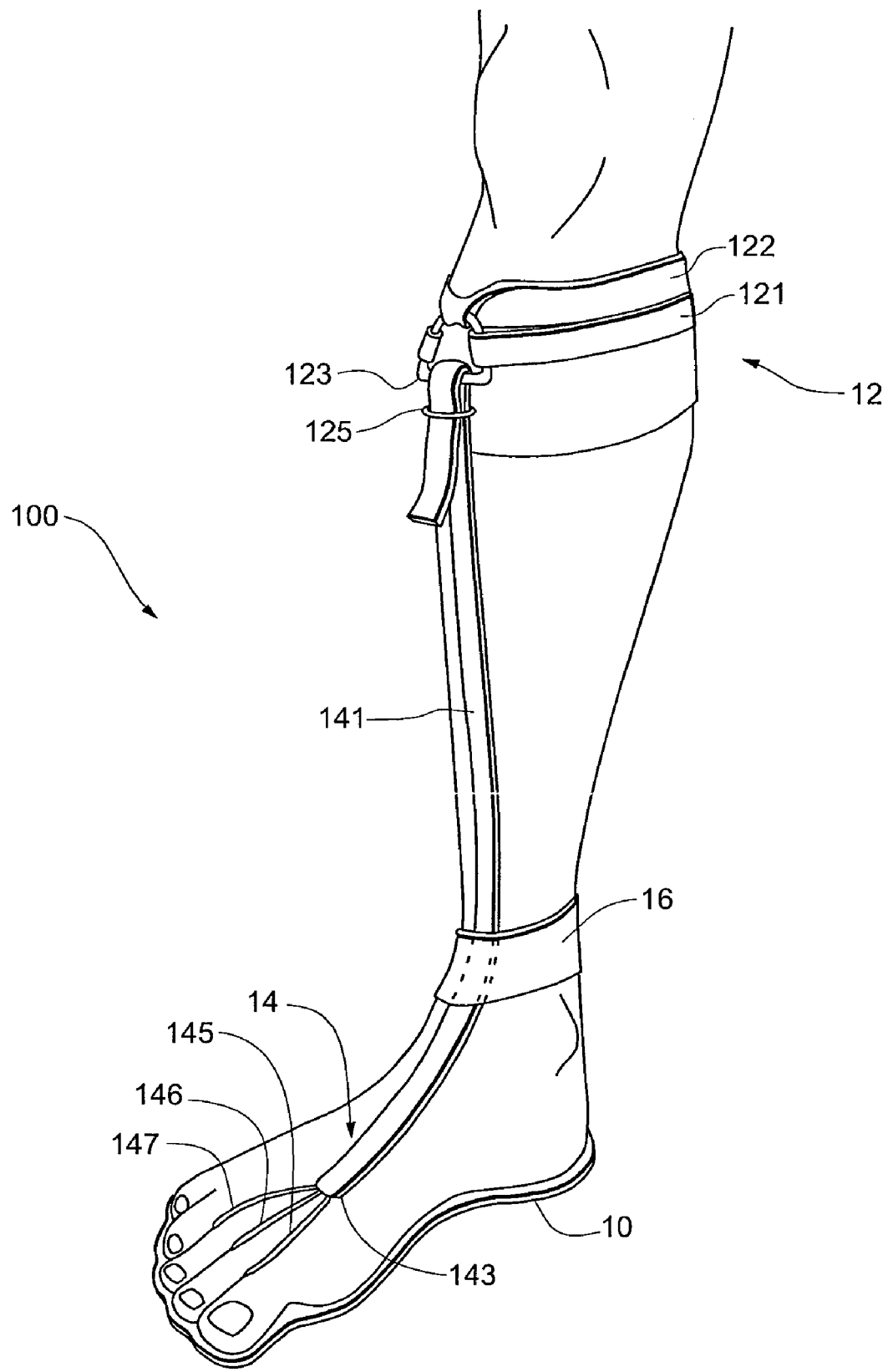
FIG. 1 is a schematic perspective view of a foot support system as it may be secured to a leg and foot of a wearer according to one embodiment of the invention.

The following detailed description should be read with reference to the drawings, in which like numerals denote like elements. The drawings, which are not to scale, depict selected embodiments and are not intended to limit the scope of the invention. It will be understood that embodiments shown in the drawings and described below are merely for illustrative purposes, and are not intended to limit the scope of the invention as defined in the claims.

FIG. 1 is a schematic perspective view of a foot support system 100 as it may be worn on a leg and foot of a person (the "wearer") according to one embodiment of the invention. FIG. 1 illustrates system 100, including a base 10 positioned beneath and adapted to receive a sole of a foot, a cuff 12 adapted to be secured to a leg near a knee of the wearer, and a support strap 14 extending between cuff 12 and base 10, a proximal end of support strap 14 being coupled to cuff 12, a distal end of support strap 14 being coupled to base 10. Cuff 12 may be secured to the leg of the wearer at, below, or above the knee, for example. Strap 14 extends between cuff 12 and base 10 to bias at least a portion of base 10 upwardly toward cuff 12.

According to the embodiment shown in FIG. 1, strap 14 may include an elastic portion 141, and a plurality of branches for coupling strap 14 to base 10. The embodiment of FIG. 1 shows strap 14 coupled to base 10 using first, second and third branches 145, 146 and 147, respectively. For example, branches 145, 146, and 147 may be coupled to a distal end of elastic portion 141, and may be adapted to extend between toes of a wearer's foot to couple strap 14 to base 10. Branches 145, 146, and 147 may be coupled to base 10 via a variety of attachment means, such as couplings 345, 346, and 347, described below with reference to FIG. 3B, or by sewing, adhesive bonding, interference fit, or any other attachment means known to those skilled in the art. In certain embodiments, branches 145, 146 and 147 may be formed of a non-compliant material, and may further include soft portions that extend between the wearer's toes, to provide comfort to the wearer. According to certain alternate embodiments of the invention, strap 14 may be coupled to base 10 using only one branch, for example, branch 245 as illustrated in FIG. 2. Other numbers of branches may also be used, for example two or four branches, without departing from the scope of the invention.

According to certain embodiments of the invention, elastic portion 141 of support strap 14 may provide a sufficient amount of tension between base 10 and cuff 12 to bias the foot of the wearer in a dorsi-flexed position, as shown in FIG. 1, while also providing sufficient elasticity to allow plantar-flexion of the foot, for example by voluntary muscle contraction. In use, strap 14 may be retained or held in relatively conforming proximity to the leg and foot of the wearer with a portion of a shoe or hosiery fitted over the foot and lower portion of the leg. Some examples of materials from which elastic portion 141 of support strap 14 may be formed include, but are not limited to, rubber and elasticized woven fabric tapes. However, any material possessing the tension and elasticity characteristics needed to provide dorsi-flexion while allowing plantar-flexion may be used for elastic portion 141. Some examples of materials from which branches 145, 146, and 147 of strap 14, may be made include, but are not limited to, leather and woven or braided fibers.

FIG. 1 illustrates an embodiment of the invention in which support strap 14 is coupled to cuff 12 by having a proximal end of support strap 14 threaded through an eye 123 of cuff 12 and secured with a clip 125. The tension provided by support strap 14 may be adjusted, for example, by varying the length of the strap 14 pulled through eye 123. According to the illustrated embodiment, cuff 12 may further include an elastic band 121, for holding cuff 12 in place, and a strain relief interface 122 adapted to be positioned between elastic band 121 and the wearer's leg. Strain relief interface 122 may cover a larger surface area of the leg than band 121 to prevent band 121 from "digging" into the wearer's leg, and to generally provide more comfort to the wearer. Strain relief interface 122 may be adapted to be positioned near a wearer's knee, which may include areas at, above, and below the knee. A wearer may decide, for example, that a particular location of cuff 12 may be more comfortable, or may provide better dorsi-flexion support. Strain relief interface 122 may, for example, comprise a flexible, tubular member that extends from slightly below the knee to slightly above the knee. The choice of location of cuff 12 upon a wearer's leg may be further influenced by aesthetic considerations, for example. Examples of materials from which strain relief interface 122 may be made include, but are not limited to, foam rubber and leather. Ends of band 121 are shown coupled to eye 123, which may in turn be coupled to interface 122. Band 121 may be fitted about the wearer's leg by inserting the foot through band 121, or band 121 may be an elongate member that includes ends (not shown) that may be wrapped about the leg and closed together by any fastening means known to those skilled in the art.

With continued reference to FIG. 1, system 100 may further include a strap holder 16 adapted to be wrapped about the wearer's leg or foot or both according to certain embodiments of the invention. Strap holder 16 is adapted to retain strap 14 in relatively conforming proximity to the leg and foot, preferably near the ankle. As with band 121, strap holder 16 may be fitted about the leg by inserting the foot through strap holder 16, or may comprise an elongate member that may include ends (not shown in FIG. 1) that may be wrapped about the leg and closed together. Examples of materials from which band 121 and strap holder 16 may be formed include, but are not limited to, plastic, leather, woven fibers, and elasticized woven fabric tapes.

FIG. 2 is a top perspective view of a foot support system 200 according to another embodiment of the invention. FIG. 2 illustrates base 10, which includes a toe edge 101, a heel edge 102, a first side edge 103 and a second side edge 104. According to some embodiments of the invention, base 10 is an insole whose edges 101, 102, 103, and 104 are all contoured to generally correspond to a wearer's foot so that the insole may conform to a sole of the wearer's foot and fit within the wearer's shoe. Such an insole may preferably be made of leather, but may also be made of any other semi-rigid material providing a comfortable interface with the sole of the foot. Alternately, base 10 may be made of a more rigid material, in part, or as a whole. One of ordinary skill in the art will recognize that a variety of semi-rigid and rigid materials may be suitable for performing the function of an insole, and hence, for forming base 10.

FIG. 2 further illustrates system 200 including a cuff 22, a support strap 24 extending between cuff 22 and base 10, and a strap holder 26. According to the illustrated embodiment, an elastic portion of strap 24 includes a proximal segment 242 and a distal segment 243; a distal portion 245 of strap 24 extends from distal segment 243 to a coupling 247 that is coupled to base 10. Distal portion 245 is shown to include an optional soft portion 29 that may extend between toes of a wearer's foot. Proximal segment 242 of the elastic portion of strap 24 is shown in FIG. 2 adjustably coupled to cuff 22 by means of buckle 223. According to certain embodiments, proximal segment 242 may include reinforcement material near the portion that engages with buckle 223. Cuff 22 is also shown to include a cushioned inner surface 222 and ends 225, 226 having mating hook-and-loop fastening surfaces to fasten cuff 22 about a leg. One of ordinary skill in the art will recognize that a variety of fastening mechanisms may be used in place of a hook-and-loop fastener and will be considered to fall within the scope of the claimed invention.

FIG. 2 also shows an embodiment of the invention in which inner surface 261 of strap holder 26 may be adapted to be at least somewhat lubricious with respect to strap 24, thereby allowing strap 24 to slide relative to strap holder 26, as indicated by double-headed arrow, "A." Strap 24 is thus adapted to slideably contact strap holder 26. For example, strap 24 may stretch in response to voluntary plantar-flexion of the foot, and may contract in response to the tension provided by strap 24, causing strap 24 to slide with respect to a portion of the inner surface 261 of strap holder 26. System 200 is also shown to include a strip 28 extending up from heel end 102 of base 10, coupling strap holder 26 to base 10. Strip 28 may be made from leather or fabric or a plastic material suitable for maintaining strap holder 26 in a desired position. The length of strip 28, for example, may be chosen to ensure that strap holder 26 retains strap 24 in relatively conforming proximity to the leg of the wearer.

Figure 3A:
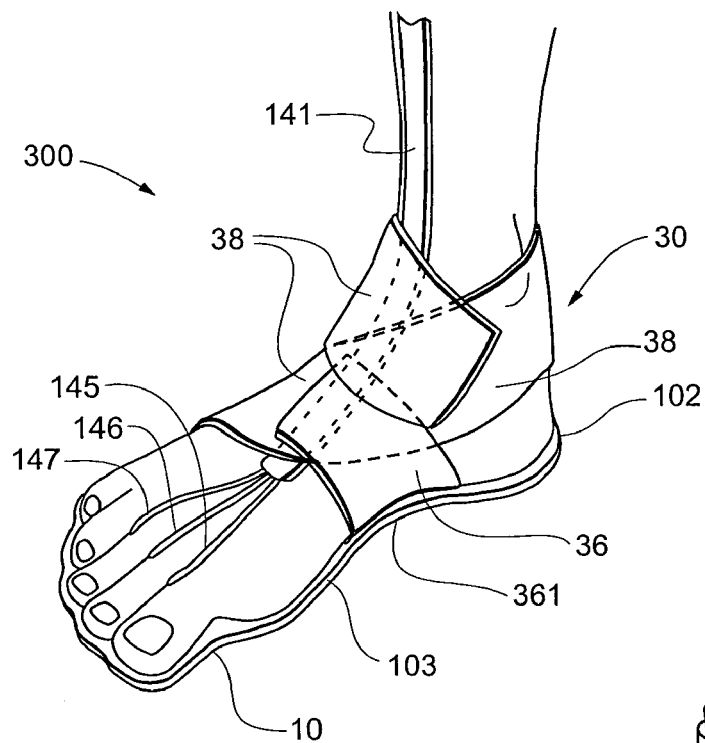
FIG. 3A is a schematic perspective view of portions of a foot support system attached to a leg and foot according to an embodiment of the invention.
Figure 3B:
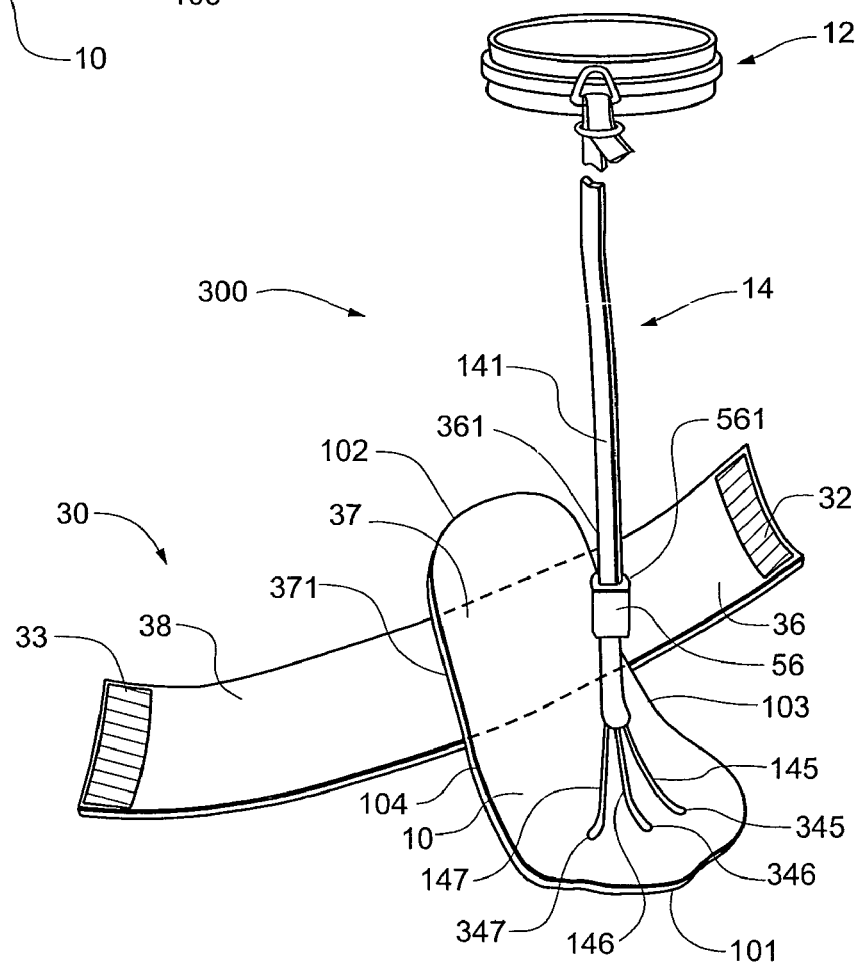
FIG. 3B is a perspective view of the foot support system of FIG. 3A.

FIG. 3A is a schematic perspective view of a foot support system 300 as it may be worn on a foot and leg of a wearer, according to certain embodiments of the invention. FIG. 3B is a perspective view of the foot support system 300 of FIG. 3A providing additional details. FIGS. 3A and 3B illustrate system 300 including some elements common to those included in systems 100 and/or 200, previously described in conjunction with FIGS. 1 and 2. FIGS. 3A and 3B illustrate an alternate embodiment of a strap holder 30 including a first strip 36 coupled to first side edge 103 of base 10 at a junction 361, and a second strip 38 coupled to second side edge 104 at a junction 371. According to the illustrated embodiment, strips 36 and 38 hold strap 14 in relatively conforming proximity to the foot and leg of the wearer. Second strip 38 may be wrapped over a dorsal aspect of the foot and about the leg, just above the foot, as shown in FIG. 3A, and first strip 36 may be wrapped over the dorsal aspect of the foot. Strip 38 may overlap on itself and may be adapted to attach to itself by means of a fastening surface 33, as shown in FIG. 3B. Likewise, strip 36 may include a fastening surface 32 and may similarly overlap on strip 38 to fasten thereto. Strips 36 and 38 may be formed of any flexible material that conforms to the foot and leg. According to an alternate embodiment, strap holder 30 may further include a base strip portion 37, shown by phantom lines in FIG. 3B, extending between first strip 36 and second strip 38. Strap holder 30 therefore need not be fixedly attached to base 10, but may instead form an independent element adapted to be wrapped around base 10, and the foot and leg as shown. Strap holder 30 may be further adapted to be removable and/or adjustable.

FIG. 3B also illustrates an embodiment of the invention in which strap 14 may be slideably engaged within a bore 561 of a guide 56. According to some embodiments of the invention, guide 56 may be positioned along a support strap proximate a strap holder, for example, strap holder 30 (FIG. 3A) or strap holder 16 (FIG. 1), to allow the support strap 14 to slide relative to the strap holder when the elastic portion of strap 14 stretches and contracts as previously described in conjunction with FIG. 2. Guide 56 may, for example, be positioned either above or beneath strap holder 16 (or 30) according to certain embodiments of the invention. According to one embodiment, bore 561 of guide 56 provides clearance between the support strap 14 and the strap holder to allow for movement of the support strap 14 relative to the strap holder. Bore 561 may form a lubricious surface within guide 56 to reduce friction with the support strap, with or without providing any clearance. Examples of materials from which guide 56 may be made include, but are not limited to, hard plastic, leather and woven or braided fibers.

Figure 4:
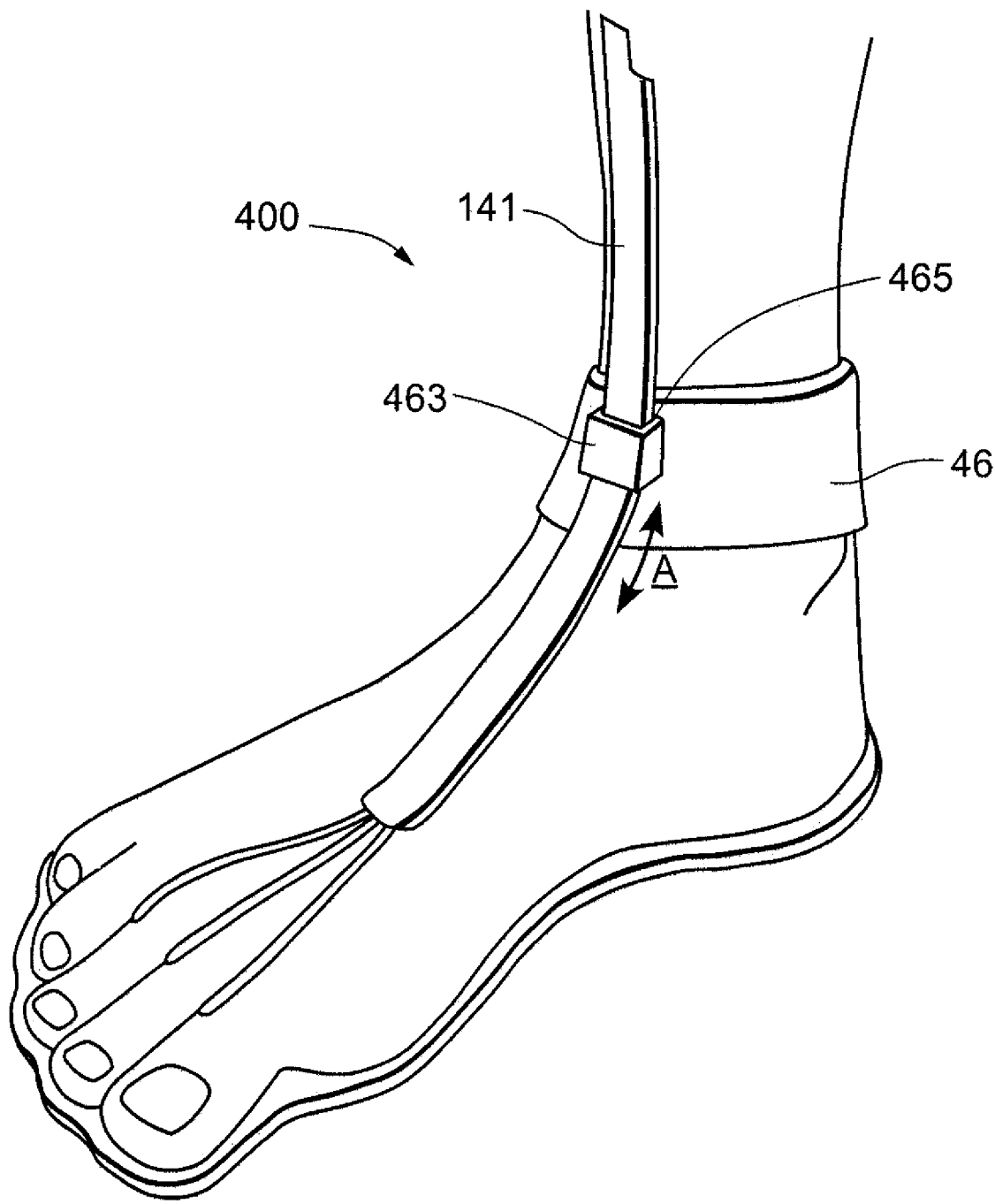
FIG. 4 is a schematic perspective view of a foot support system secured to a leg and foot of a wearer according to an embodiment of the invention.

FIG. 4 is a schematic perspective of a foot support system 400 as it may be worn on a leg and foot of a wearer, illustrating an alternate embodiment of a strap holder. FIG. 4 illustrates a strap holder 46 and a guide 463. According to the illustrated embodiment, guide 463 may include a bore 465 through which strap 14 may be slideably guided. Although guide 463 is shown coupled to an exterior surface of strap holder 46 in the embodiment of FIG. 4, it may alternately be disposed on an internal surface of strap holder 46. According to one embodiment, bore 465 of guide 463 provides clearance between the support strap 14 and the strap holder 46 to facilitate sliding of the support strap 14 relative to the strap holder 46. Bore 465 may include a lubricious surface to reduce friction with the support strap, with or without providing any clearance. Guide 463 may be a loop integrally formed in strap holder 46, or may be a separate component attached to strap holder 46 by means of sewing or adhesive bonding, or by any other method known to those skilled in the art. Exemplary materials from which guide 463 may be made include, but are not limited to, hard plastic, leather and woven or braided fibers.

Thus, embodiments of a DEVICE FOR TREATING FOOT DROP are disclosed. One skilled in the art will appreciate that the invention can be practiced with embodiments other than those disclosed. The disclosed embodiments are presented for purposes of illustration and not limitation, and the invention is limited only by the claims that follow.

What is claimed is:

1. A foot support system, comprising:
   a base adapted to receive a sole of a foot, the base including a toe edge, a heel edge, a first side edge extending between the toe and heel edges, a second side edge extending between the toe and heel edges, and an upper surface extending between the toe and heel edges and the first and second side edges;
   a cuff adapted to be secured to a first portion of a leg near a knee of the leg; and
   a strap including
      an elastic portion having a proximal segment and a distal segment, the proximal segment adapted to be coupled to the cuff, and
      a plurality of branches coupling the distal segment of the elastic portion of the strap to the base near the toe edge of the base, the branches spaced to allow passage of a toe between adjacent branches.

2. The system of claim 1, wherein the plurality of branches comprises three generally non-compliant branches.

3. The system of claim 1, wherein at least one branch includes a soft portion.

4. The system of claim 1, wherein the base comprises an insole shaped and contoured to generally correspond to a sole of a foot.

5. The system of claim 4, wherein the insole is formed at least partially of leather.

6. The system of claim 1, wherein the cuff includes an adjustable band to hold the cuff near the knee of the leg.

7. The system of claim 1, wherein the cuff includes a band to hold the cuff near the knee of the leg, and a strain relief interface positioned between the band and the leg.

8. The system of claim 7, wherein the strain relief interface includes a cushioned interface with the leg.

9. The system of claim 1, wherein the cuff further comprises:
   an eye disposed on an anterior portion of the cuff to receive a proximal portion of the strap; and
   a clip for securing the proximal portion of the strap adjacent the eye.

10. The system of claim 9, wherein the cuff further includes an elastic band, the elastic band having a first end and a second end, each end attached to the eye.

11. The system of claim 1, wherein the cuff further comprises:
   a buckle disposed on an anterior portion of the cuff to receive a proximal portion of the strap.

12. A foot support system, comprising:
   a base adapted to receive a sole of a foot, the base including a toe edge, a heel edge, a first side edge extending between the toe and heel edges, a second side edge extending between the toe and heel edges, and an upper surface extending between the toe and heel edges and the first and second side edges;
   a cuff adapted to be secured to a first portion of a leg near a knee of the leg;
   a strap including an elastic portion having a proximal segment and a distal segment, the proximal segment adapted to be coupled to the cuff, the distal segment adapted to be coupled to the base near the toe edge of the base; and
   a strap holder adapted to be secured to a second portion of the leg near an ankle of the leg to retain the strap near the second portion of the leg.

13. The system of claim 12 wherein the strap holder is further adapted to allow the strap to slide relative to the strap holder.

14. The system of claim 13 wherein the strap holder includes a lubricious surface adapted to slidably engage a portion of the strap.

15. The system of claim 13 wherein the strap is adapted to slide relative to the strap holder along a length of the leg in response to the strap stretching or contracting between the base and the cuff.

16. The system of claim 12, wherein the strap holder is coupled to the base near the heel edge of the base.

17. The system of claim 12, wherein the strap holder includes a first strip extending from the first side edge of the base and a second strip extending from the second side edge of the base, the first and second strips being adapted to wrap over a dorsal aspect of the foot.

18. The system of claim 17, further comprising a third strip extending between the first and second strips beneath the base near the heel edge of the base.

19. The system of claim 12, wherein the strap holder is coupled to the base via a strip extending from the heel edge of the base to a posterior portion of the strap holder.

20. A foot support system, comprising:
- a base adapted to receive a sole of a foot, the base including a toe edge, a heel edge, a first side edge extending between the toe and heel edges, a second side edge extending between the toe and heel edges, and an upper surface extending between the toe and heel edges and the first and second side edges;
- a cuff adapted to be secured to a first portion of a leg near a knee of the leg;
- a strap including an elastic portion having a proximal segment and a distal segment, the proximal segment adapted to be coupled to the cuff, the distal segment adapted to be coupled to the base near the toe edge of the base and further adapted to extend between a first and second toe of the foot;
- a strap holder adapted to be secured to a second portion of the leg near an ankle of the leg to retain the strap near the second portion of the leg; and
- a guide slideably coupled to a portion of the strap, the guide adapted to facilitate movement of the strap along a length of the leg relative to the strap holder when the elastic portion of the strap stretches and contracts between the base and the cuff, a portion of the guide being positioned between the strap holder and the strap.

* * * * *